United States Patent
Kamo et al.

(10) Patent No.: US 9,486,398 B2
(45) Date of Patent: Nov. 8, 2016

(54) COMPOSITION (71) Applicant: J-OIL MILLS, INC., Tokyo (JP)

(72) Inventors: Shuichi Kamo, Tokyo (JP); Toshiro Sato, Tokyo (JP); Rumi Kawahara, Tokyo (JP); Shunsuke Suzuki, Tokyo (JP)

(73) Assignee: J-Oil Mills, Inc., Tokyo (JP)

( * ) Notice: Subject to any disclaimer, the term of this patent is extended or adjusted under 35 U.S.C. 154(b) by 151 days.

(21) Appl. No.: 14/596,698

(22) Filed: Jan. 14, 2015

(65) Prior Publication Data

US 2015/0126454 A1 May 7, 2015

Related U.S. Application Data (63) Continuation of application No. PCT/JP2013/063553, filed on May 15, 2013.

(30) Foreign Application Priority Data

Jul. 24, 2012 (JP) .................................. 2012-164083

(51) Int. Cl.

| *A61K 8/67* | (2006.01) |
|---|---|
| *A61K 8/63* | (2006.01) |
| *A61K 8/65* | (2006.01) |
| *A61K 8/97* | (2006.01) |
| *A61K 31/122* | (2006.01) |
| *A61K 36/48* | (2006.01) |
| *A61K 31/56* | (2006.01) |
| *A61K 8/34* | (2006.01) |
| *A61Q 19/00* | (2006.01) |

(52) U.S. Cl.
CPC ................ *A61K 8/67* (2013.01); *A61K 8/345* (2013.01); *A61K 8/63* (2013.01); *A61K 8/65* (2013.01); *A61K 8/97* (2013.01); *A61K 31/122* (2013.01); *A61K 31/56* (2013.01); *A61K 36/48* (2013.01); *A61Q 19/00* (2013.01); *A61Q 19/007* (2013.01); *A61Q 19/008* (2013.01); *A61K 2800/59* (2013.01)

(58) Field of Classification Search
CPC ....................................................... A61K 8/67
See application file for complete search history.

(56) References Cited

U.S. PATENT DOCUMENTS

2006/0275862 A1   12/2006   Watanabe et al.

FOREIGN PATENT DOCUMENTS

| JP | H05155803 A | 6/1993 |
|---|---|---|
| JP | H0873396 A | 3/1996 |
| JP | H10029911 | 2/1998 |
| JP | 2000093121 A | 9/1998 |
| JP | H10295393 A | 11/1998 |
| JP | H11035445 | 2/1999 |
| JP | H1192414 A | 4/1999 |
| JP | 2001136959 A | 5/2001 |
| JP | 2004250372 A | 9/2004 |
| JP | 2005137201 A | 6/2005 |
| JP | 2006166807 A | 6/2006 |
| JP | 2006315957 A | 11/2006 |
| JP | 2008050297 A | 3/2008 |
| JP | 2008099562 A | 5/2008 |
| WO | 2008155890 A1 | 12/2008 |
| WO | 2010150612 A1 | 12/2010 |
| WO | 2012111187 A1 | 8/2012 |

OTHER PUBLICATIONS

Vasantha Rupasinghe, H.P. et al, "Soyasapogenol A and B Distribution in Soybean (Glycine max L. Merr.) in Relation to Seed Physiology, Genetic Variability, and Growing Location", Journal of Agricultural and Food Chemistry, 2003, 51, pp. 5888-5894.
International Search Report, PCT/JP2013/063553 dated Aug. 13, 2013, 10 pages.

*Primary Examiner* — Amber D Steele
(74) *Attorney, Agent, or Firm* — Edell, Shapiro & Finnan, LLC

(57) ABSTRACT

A composition that is useful in a skin function improving agent includes at least two of the following: vitamin K, a sapogenol, and a collagen hydrolysate. This composition can be used in a skin function improving agent and is particularly useful in a skin function improving agent for inhibiting transdermal moisture loss and/or for retaining the moisture in the stratum corneum.

8 Claims, 3 Drawing Sheets

COMPOSITION

TECHNICAL FIELD

The present invention relates to a novel composition containing at least two of vitamin K, sapogenol, and collagen hydrolysate, and more particularly relates to the composition that is useful as a skin function improving agent.

BACKGROUND

The skin is mainly divided into the epidermis, dermis, and subcutaneous tissue. The epidermis is further divided into, from the surface, the sebaceous membrane, stratum corneum, stratum *granulosum*, stratum *spinosum*, and stratum basale.

The sebaceous membrane consists of the sebum secreted from the sebaceous gland, the sweat gland, or the like. Sebum plays a role in preventing water loss. Transepidermal water loss (TEWL) means the amount of water that is volatilized unconsciously from the body through the stratum corneum. The amount of sebum and TEWL are inversely correlated; for example, if the amount of sebum is large, TEWL is decreased. A higher TEWL value means decreased barrier function of the stratum corneum. As a result, the skin becomes grainy or dry, resulting in rough skin. If secretion of sebum is too much, the skin becomes oily and sticky and the sebum is changed to an irritant, which is a factor for inflammation and acne of the skin. Moderate secretion of sebum is needed so that the sebaceous membrane can perform an important function.

In the stratum corneum under the sebaceous membrane, corneocytes filled with hard keratin proteins are stacked in about 1 mm layers. Each corneocyte is linked by intercellular lipids. The structure of the stratum corneum is so compact that water and fluid in the body do not leak out. The phenomenon that basal cells divide once when corneocytes in the top layer of the stratum corneum is shed is referred to as keratinization. As a result of the fact that old keratin is shed to be replaced by a new corneocyte, the functions of the stratum corneum are maintained and the thickness of the epidermis is kept constant.

Even when corneocytes are formed by hard keratin proteins, softness of the skin needs to be maintained to some extent. To do this, the stratum corneum contains 20% to 30% of moisture. If moisture is lost, keratin becomes hard and the skin becomes dry.

Natural moisturizing factor (NFM) plays a role in retaining the moisture in the stratum corneum. NFM consists of amino acid, PCA (pyrrolidone carboxylic acid), lactate, urea, and the like. NMF having high hydrophilicity is helpful in retaining moisture.

Intercellular lipids are lipids formed by keratinization of keratinocytes. Intercellular lipids consist of ceramides, cholesterol, cholesteryl ester, and the like. Ceramide and free fatty acids such as linoleic acid contained therein play a role in retaining moisture and the barrier function of the stratum corneum. If an abnormality occurs in intercellular lipids, the water-retaining function is lost, the skin becomes dry, and inflammation becomes likely to occur.

The dermis is positioned under the stratum basale of the epidermis, and is a layer with a thickness of 2 mm consisting of protein fibers that are constituted of collagen and elastin and substrates. Collagen plays a role in providing taut skin and supporting elastin. Elastin provides elasticity to the skin even though by about 2%. Substrates filling the space between protein fibers are extracellular matrix components such as proteoglycan and hyaluronic acid. Intercellular lipids retain most of the moisture in the dermis. In the skin with youthfulness maintained, production of extracellular matrix components is promoted, and the elasticity, water retention, and tautness of the skin are kept.

Internal factors such as aging, disease, stress, and hormone abnormalities and external factors such as dryness and ultraviolet rays decrease moisture and extracellular matrix (e.g., collagen, hyaluronic acid) from dermal tissues and decrease the functions of the epidermis and dermis of the skin. Decreased skin functions appear as skin wrinkles, decreased elasticity (slackness), or rough skin.

To solve problems regarding beauty including skin aging and rough skin, functional foods for ingestion of various active ingredients and cosmetic compositions have been developed and marketed.

JP 2008-99562 A (Skin-Beautifying Oral Composition) discloses a skin-beautifying oral composition containing royal jelly, isoflavone, and collagen. This disclosure provides food having skin-beautifying effect of improving softness of the skin and fixing up skin texture.

JP 2000-93121 A (Beauty Food) discloses beauty food containing at least one of kuma bamboo grass (*Sasa albomarginata*), five-leaf ginseng (*Gynostemma pentaphyllum*), Siberian ginseng (*Acanthopanax senticosus* Harms), betaine, and soyasaponin, and a collagen peptide. This disclosure provides a beauty food enabling the restoration of skin tension and gloss and the maintenance of a moist and young bare skin.

JP 11-35445 A (Cosmetic Composition) discloses a cosmetic composition obtained by combining soyasaponin with at least one of hyaluronic acid, salt of hyaluronic acid, collagen, and elastin. This disclosure can enhance skin brightness and maintain healthy and beautiful skin by the synergy of the effect of preventing skin aging by inhibiting the production of subcutaneous lipid peroxide by the combination of soyasaponin with the moisture retention effect by the combination of at least one of hyaluronic acid, salt of hyaluronic acid, collagen, and elastin.

JP 10-29911 A (Cosmetic Material Composition) discloses a cosmetic material composition containing an extract of soybean and adzuki bean powder as essential active ingredients. This disclosure describes a reduction of the abnormality of the skin with increased lipid peroxide in the body, i.e., somber and stained skins, rough skin, and the like.

JP 2004-250372 A (Skin Aging Inhibitor/Improver and/or Rough Skin Inhibitor/Improver Kit) discloses a drink containing an active ingredient effective for beautifying skin and alcohol, and a skin aging inhibitor/improver and/or rough skin inhibitor/improver kit including the drink and a soybean germ extract-containing external preparation. The active ingredient effective for beautifying skin is selected from biological collagen synthesis promoter, abnormal protein remover, female hormone-like agent, and moisturizer.

SUMMARY

It is an object of the present invention to provide a novel composition that is highly effective in improving the skin function.

By diligently considering the above problem, the present inventors have successfully increased the effect on the skin improving function by the combination of at least two specified components compared with the single use, and completed the present invention.

In other words, the present invention provides a composition containing at least two components selected from the group consisting of vitamin K, sapogenol, and collagen hydrolysate.

The prior art mentions a composition containing saponin or collagen hydrolysate, but does not mention a composition containing at least two components selected from the group consisting of vitamin K, sapogenol, and collagen hydrolysate, like the present application invention. The fact that combination of at least two components has synergistic effects on the skin improving function is also not known at all.

A composition of the present invention preferably essentially contains the vitamin K.

The vitamin K is preferably vitamin K2.

The vitamin K2 is particularly preferably menaquinone-7.

The sapogenol is, for example, derived from soybean.

In the collagen hydrolysate, the content of peptide having a molecular weight from 200 to less than 3,000 is preferably not less than 40% by mass.

The present invention also provides a skin function improving agent with the active ingredient of the above composition.

The skin function improving agent contains the vitamin K and the sapogenol, and is for inhibiting transdermal moisture loss.

The skin function improving agent contains the vitamin K and the collagen hydrolysate, and is for retaining the moisture in the stratum corneum.

As mentioned above, decreases in water retained on each layer of dermal tissues are associated with decreased skin functions. According to the present invention that essentially contains at least two components selected from the group consisting of vitamin K, sapogenol, and collagen hydrolysate, synergistic effects that cannot be achieved by a single component regarding the water retention in dermal tissues can be obtained, although the reason is not clear.

A composition of the present invention has a skin function improving function. Therefore, the composition of the present invention is useful as a skin function improving agent. The skin function improving agent is provided as functional foods, supplements, pharmaceuticals, and/or cosmetics.

When the skin function agent contains the vitamin K and the sapogenol, effects of inhibiting the transdermal moisture loss are exerted. When the skin function agent contains the vitamin K and the collagen hydrolysate, effects of retaining the moisture in the stratum corneum are exerted.

Since the above mentioned three components are derived from natural plants and animals, it is likely that they have few side effects. Long-term intake or application of the composition of the present invention can provide excellent effects.

BRIEF DESCRIPTION OF DRAWINGS

FIG. 2B is a view showing changes in the keratin moisture, like FIG. 2A. Comparison of Example 2 (menaquinone-7+soyasapogenol) with Comparative Example 1 (menaquinone-7) and Comparative Example 3 (soyasapogenol) reveals that menaquinone-7 has no stratum corneum water-retaining function, while the combination of soyasapogenol and menaquinone-7 exerts a keratin water-retaining function similar to that by soyasapogenol.

FIG. 2C is a view showing changes in the keratin moisture, like FIG. 2A. Comparison of Example 3 (collagen hydrolysate+soyasapogenol) with Comparative Example 2 (collagen hydrolysate) and Comparative Example 3 (soyasapogenol) reveals that collagen hydrolysate has no stratum corneum water-retaining function, while the combination of soyasapogenol and collagen hydrolysate exerts a keratin water-retaining function.

DETAILED DESCRIPTION

One embodiment of the composition of the present invention will be described in detail below. Vitamin K that can be used for the composition of the present invention includes vitamin K1 to K3. Vitamin K1 (also referred to as phylloquinone) is abundantly contained in green and yellow vegetables, pulse, vegetable oil, seaweed, seafood, and the like. Vitamin K2 (also referred to as menaquinone) is produced by microorganisms, and is abundantly contained in fermented soybeans and dairy products such as cheese. Vitamin K2 is also produced by intestinal bacteria. Depending on the length of a side-chain isoprenoid group attached to the naphthoquinone skeleton, homologs of vitamin K2 from menaquinone-4 (MK-4) to menaquinone-15 (MK-15) exist. For example, MK-6 to MK-9 are abundantly contained in cheese and MK-7 is abundantly contained in fermented soybeans. Vitamin K3 (also referred to as menadione) is a complex.

There is no particular limitation on the manufacturing method of each vitamin K. Commercial vitamin K can also be used without limitation.

Vitamin K1 is extracted and purified by publicly known methods (for example, JP 5-155803 A) from green *perilla, perilla* (*Perilla frutescens*), Jew's marrow, parsley, garland

*chrysanthemum*, Komatsuna (*Brassica rapa* var *perviridis*), spinach, Japanese honewort, alfalfa, leaf of Asian Hazel, leaf of chestnut, spear of barley, spear of wild oat, cabbage, broccoli, cauliflower, tomato, vegetable oil (soybean oil, rapeseed oil, sesame oil, peanut oil, corn oil, safflower oil, sunflower oil, rice bran oil, and olive oil), and the like. Vitamin K1 can also be obtained from synthesis. Vitamin K1 is fat-soluble, pale yellow, oily, and stable for heat, but unstable for light. Vitamin K1 may be an oxide.

Vitamin K2 is fermented and produced by microorganisms such as Hay *bacillus* (*Bacillus subtilis* var. *natto*) in accordance with, for example, methods mentioned in JP 08-073396 A, JP 11-92414 A, JP 10-295393 A, JP 2001-136959 A, and the like.

Vitamin K3 can be obtained by chemosynthesis.

Intake of large amount of vitamin K3 raises a concern of side effects. Therefore, from our previous eating experience, vitamin K1 that is extracted and purified from vegetables and vitamin K2 that is extracted from fermented products using Hay *bacillus* (*Bacillus subtilis* var. *natto*) and the like are preferable in terms of higher safety. Vitamin K2 that can be produced inexpensively and easily is more preferable. Menaquinone-4 that is approved as a food additive and/or menaquinone-7 that is utilized as a food material are particularly preferable.

The content of vitamin K in the composition of the present invention varies depending on the use or form of the composition, but may be usually 0.00001 to 99% by weight, preferably 0.00005% to 70% by weight, more preferably 0.0001 to 60% by weight, and still more preferably 0.01 to 50% by weight. If the content of vitamin K is 0.00001% by weight or less, synergistic effects by using in combination with other components (collagen hydrolysate and/or sapogenol) may not be obtained.

Saponin is an amorphous glycoside which is abundantly present in soybeans, adzuki beans, olive, and the like. Saponin is named since it has a hydrophobic portion and a hydrophilic portion and forms persistent bubbles when mixed with water and shaken. Saponin is broadly classified into steroid saponin and triterpenoid saponin according to the type of aglycone. The soyasaponin contained abundantly in soybeans, particularly in a soybean hypocotyl is a kind of the triterpenoid saponin. Sapogenol means the aglycone in which the part or whole of sugar chain residues are removed from the saponin glycoside derived from soybeans, adzuki beans, or olive. Sapogenol used for the composition of the present invention is preferably derived from soybeans.

Soyasapogenol derived from soybeans includes soyasapogenol A, which can be obtained from soyasaponin Aa, Ab, Ac, Ad, Ae, Af, Ag, and Ah (soyasaponin A group glycoside), and soyasapogenol B, which can be obtained from soyasaponin I, II, III, IV, and V (soyasaponin B group glycoside).

Soyasapogenol can be obtained by removing the part or whole of sugar chains from soyasaponin glycoside. Specifically, soyasaponin glycoside is subjected to enzymatic reaction with glycosidase (US 2006/0275862), high temperature and pressure treatment (WO 2008/155890), or fermentation treatment. Soyasapogenol may be obtained by chemosynthesis (JP 2005-137201 A). The above mentioned literatures will be inserted into the present description for reference.

Soyasapogenol having part of sugar chain residues (e.g., 3-O-D-glucuronopyranosyl soyasapogenol B, 3-O-D-glucuronopyranosyl soyasapogenol A) can be obtained by partial acid decomposition of soyasaponin glycoside. Specifically, after dissolving the soyasaponin glycoside into an organic solvent such as ethanol, methanol, and butanol, an acid such as sulfuric acid and hydrochloric acid is added. As another method, soyasaponin glycoside is added to and dissolved into a reaction solvent obtained by diluting the acid with water, ethanol, methanol, or the like. The acid decomposition is started by heating the solution to which the acid is added. An acid decomposition temperature is appropriately selected based on the type and concentration of the acid, a degree of the partial decomposition, and the like. A degree of progress of the partial decomposition is detected by using an appropriate detector (e.g., chromatography), and when the predetermined degree of decomposition is achieved, the solution is neutralized using a base such as sodium hydroxide. The solid phase is collected by subjecting the neutralized product to centrifugation, filtration, or the like. Apart from the desired soyasapogenol, the collected product can sometimes contain conventional soyasapogenol, raw material glycoside, protein, oligosaccharide, and the like as impurities, and thus an appropriate purification (e.g., column chromatography) may be performed to purify objects.

Soyasaponin glycoside itself can be extracted from the cotyledon, germ, or whole grains of soybeans by publicly known methods. Specifically, soyasaponin glycoside is extracted and purified from the cotyledon, germ, or whole grains of soybeans by the method mentioned in JP 03-75939 X, and the like. Commercial soyasaponin glycoside can be used without particular limitation.

The content of sapogenol in the composition of the present invention varies depending on the use or form of the composition, but may be usually 0.00002 to 99% by weight, preferably 0.0001% to 70% by weight, more preferably 0.005 to 60% by weight, and still more preferably 0.01 to 50% by weight. If the content of sapogenol is 0.00002% by weight or less, synergistic effects by using in combination with other components (vitamin K and/or collagen hydrolysate) may not be obtained.

Collagen is a fibrous protein having a molecular weight of about 300,000 having strong rigidity like steel. Collagen is abundantly contained in the dermis of the skin, tendon, artery, cartilage, and the like of animals such as mammal, bird, and fishes. Collagen can be extracted by washing the dermis of the above mentioned animals and subjecting it to an alkali treatment and neutralization.

Collagen hydrolysate can be obtained by degenerating collagen by heat to make gelatin and further hydrolyzing gelatin so that the molecular weight is as small as thousands to hundreds. For hydrolysis reaction, usually proteases such as trypsin, chymotrypsin, and subtilisin are used. The reaction conditions such as reaction temperature, reaction time, and pH are appropriately adjusted depending on enzymes used or amount. After the end of hydrolysis, heating to inactivate enzymes and cooling are carried out, and then filtration and drying are performed appropriately. A commercial product of collagen hydrolysate (e.g., product name: collagen tripeptide, JELLICE Co., Ltd.) can be used.

Collagen hydrolysate usually becomes a peptide mixture having a molecular weight distribution of 100 to 10,000. The content of tripeptide having a molecular weight of 200 to 1,000 is usually 5 to 30% by mass.

In collagen hydrolysate used for the present invention, the content of peptide having a molecular weight from 200 to less than 3,000 is preferably not less than 40% by mass, more preferably not less than 50% by mass, and still more preferably not less than 60% by mass.

The content of collagen hydrolysate in the composition of the present invention varies depending on the use or form of the composition, but may be usually from 0.00003 to 99% by weight, preferably from 0.0003% to 95% by weight, more preferably from 0.003 to 90% by weight, and still more preferably from 0.03 to 85% by weight. If the content of collagen hydrolysate is not more than 0.00003% by weight, synergistic effects by using in combination with other components (vitamin K and/or sapogenol) may not be obtained.

Figure 1A:
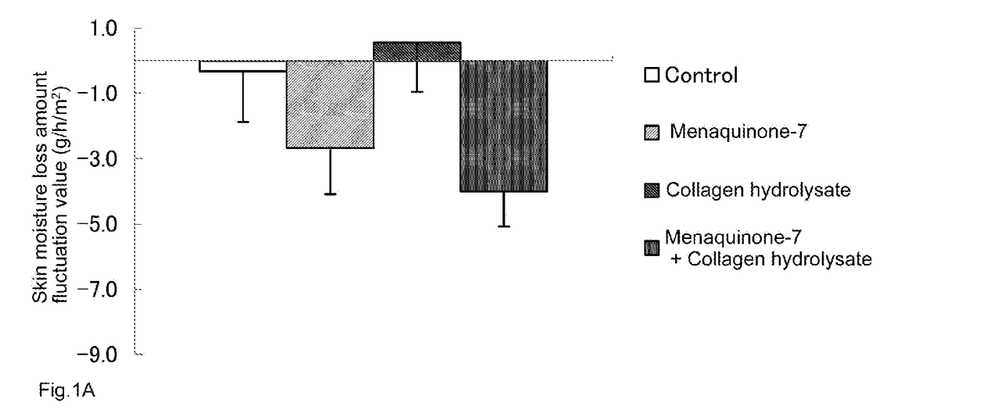
FIG. 1A is a view showing effects when the composition of the present invention was used as a skin function improving agent. The view shows the skin moisture loss amount fluctuation values (difference in the amount on day 28 after administration to the day before test substance administration) in Example 1 (menaquinone-7+collagen hydrolysate), Comparative Example 1 (menaquinone-7), and Comparative Example 2 (collagen hydrolysate). Comparison of Example 1 with Comparative Example 1 and Comparative Example 2 reveals that the combination of menaquinone-7+collagen hydrolysate exerts the synergistic effects on inhibiting the skin moisture loss.
Figure 1B:
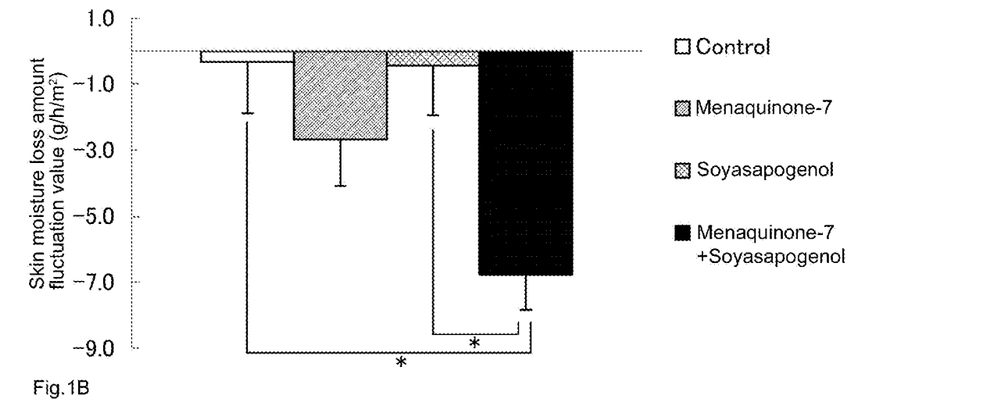
FIG. 1B is a view showing the skin moisture loss amount fluctuation values, like FIG. 1A. Example 2 (menaquinone-7+soyasapogenol) exerts more marked synergistic effects on inhibiting the skin moisture loss, compared with Comparative Example 1 (menaquinone-7) and Comparative Example 3 (soyasapogenol).
Figure 1C:
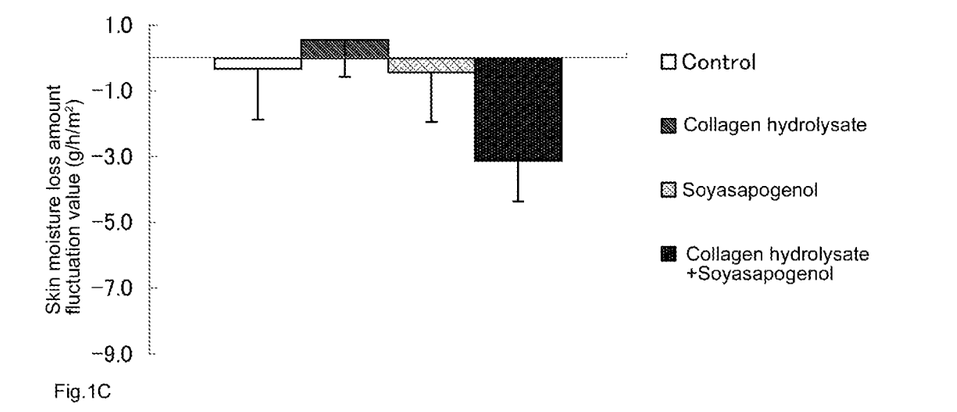
FIG. 1C is a view showing the skin moisture loss amount fluctuation values, like FIG. 1A. Example 3 (collagen hydrolysate+soyasapogenol) exerts more synergistic effects on inhibiting the skin moisture loss, compared with Comparative Example 2 (collagen hydrolysate) and Comparative Example 3 (soyasapogenol).

The composition of the present invention exerts a function of inhibiting the moisture loss from the sebaceous membrane (skin barrier function) as seen in FIGS. 1A to 1C by containing at least two of the above mentioned essential three components. As seen in FIGS. 1A and 1B, essentially containing vitamin K2 is preferable in terms of improvement in the skin barrier function. As seen in FIG. 1B, essentially containing vitamin K2 and soyasapogenol is preferable in terms of further improvement in the skin barrier function.

Figure 2A:
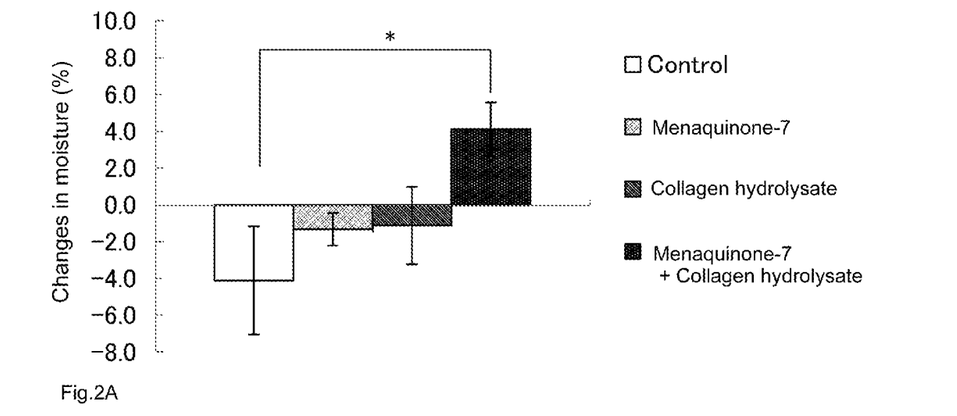
FIG. 2A is a view showing effects when the composition of the present invention is used as a skin function improving agent. The view shows the keratin moisture fluctuation values (difference in the moisture on day 28 after administration to the day before test substance administration) in Example 1 (menaquinone-7+collagen hydrolysate), Comparative Example 1 (menaquinone-7), and Comparative Example 2 (collagen hydrolysate). Comparison of Example 1 with Comparative Example 1 and Comparative Example 2 reveals that the use of menaquinone-7 or collagen hydrolysate alone has no function of keratin water retention (moisture retention), while the combination of menaquinone-7+ collagen hydrolysate has such function.
Figure 2B:
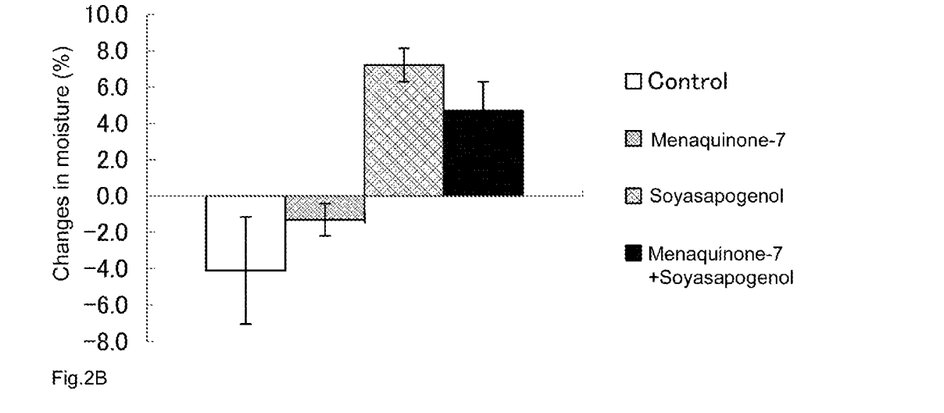
Figure 2C:
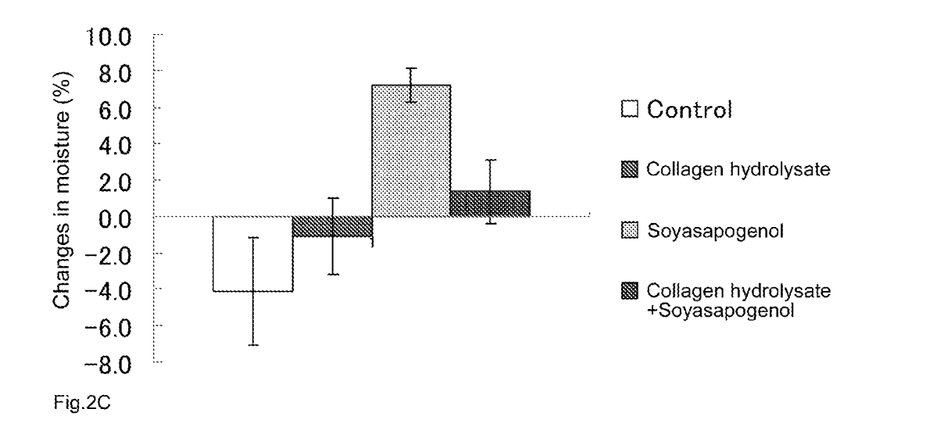

The composition of the present invention exerts a function of retaining the moisture in the stratum corneum (moisture-retaining function) as seen in FIGS. 2A to 2C by containing at least two of the above mentioned essential three components. As seen in FIG. 2A, the use of vitamin K or collagen hydrolysate alone does not exert the moisture-retaining function, while the combination of vitamin K and collagen hydrolysate exerts the moisture-retaining function.

The composition of the present invention is manufactured by appropriately combining aids or accessory components publicly known in the fields of functional foods, supplements, pharmaceuticals, and cosmetics.

The composition of the present invention can be expected to have a transdermal moisture loss-inhibiting function and a function of retaining the moisture in the stratum corneum. The composition of the present invention is provided as a functional food or supplement that retains skin moisture and improves the status of the skin such as skin wrinkles, slackness, and rough skin based on the moisture retention.

Orally taking the composition of the present invention exerts beautifying effects intended for retaining skin moisture and improving rough skin. These effects are functions of cosmetics intended for beautifying, and therefore, the composition of the present invention can be said as orally taken cosmetics.

When the composition of the present invention is used as a functional food or supplement that improves skin functions, in addition to the essential components, materials used for general purpose as additives of supplements may be added. For example, depending on the form of the orally-administered agent, diluent for general-purpose use; disintegrant; binder; lubricant; pH adjuster; cooling agent; suspending agent; emulsifier; viscous agent; solubilizer; antioxidant; coating agent; plasticizer; surfactant; corrigent; edulcorant; acidulant and the like such as citric acid; water; flavor; coloring agent; vitamins such as vitamin A, biotin, vitamin B1, vitamin B2, vitamin B6, vitamin B12, vitamin C, vitamin D, vitamin E, vitamin P, folic acid, inositol, pantothenic acid, and niacin; minerals such as calcium, potassium, sodium, phosphorus, sulfur, iron, and zinc; xanthine derivative; protein; amino acids such as glycine, alanine, proline, arginine, and glucosamine; plant extract such as rose extract; fatty acids such as oleic acid, linoleic acid, α-linolenic acid, γ-linolenic acid, arachidonic acid, eicosapentaenoic acid, docosahexaenoic acid, and cholesterol; fatty alcohol; water-soluble polymer; saccharides such as oligosaccharide, fructose, and lactose; dietary fibers such as insoluble dietary fiber, water-soluble dietary fiber, chitin, and chitosan; ceramide; glucosamine; N-acetylglucosamine; hyaluronic acid; chondroitin sulfate; polyphenol; coenzyme Q10, and the like can be added in the qualitative and quantitative range that does not impair the advantageous effects of the invention.

To use the composition of the present invention as a functional food or supplement, it is processed into an orally-administered agent such as, dusting powder, powder, granule, capsule, pill, tablet, chewable tablet, drop, biscuit, jelly, gel, syrup, and solution. Since sapogenol is powder, the form of tablet is desirable.

For the intake of the composition of the present invention when used as a functional food or supplement, the intake of vitamin K per day is preferably 0.01 to 50 mg, more preferably 0.01 to 1 mg, by considering symptoms and safety. The intake of sapogenol per day is preferably 0.1 to 100 mg, and more preferably 5 to 50 mg. The intake of collagen hydrolysate per day is preferably 0.1 to 15 g, and more preferably 1 to 10 g.

The composition of the present invention may be directly added to raw materials when general processed food such as bread, rice, soup, side dish, confectionery, and candy is processed.

When the composition of the present invention is used as a pharmaceutical that improves skin functions, in addition to the essential components, materials used for general purpose as aids to pharmaceuticals may be added. For example, depending on the dosage form and administration method, diluent for general-purpose use, disintegrant, binder, lubricant, vitamin, xanthine derivative, amino acid, pH adjuster, cooling agent, suspending agent, viscous agent, solubilizer, antioxidant, coating agent, plasticizer, surfactant, water, alcohol, water-soluble polymer, edulcorant, corrigent, acidulant, flavor, coloring agent, and the like can be added in the qualitative and quantitative range that does not impair the advantageous effects of the invention.

To use the composition of the present invention as a pharmaceutical, it is processed into the forms of orally-administered agents such as solid preparation like solution, powder, granule, capsule, pill, tablet, chewable tablet, and drop and such as solution like drinkable preparation, pharmaceutical solution, suspension, emulsion, syrup, and dry syrup, or of transdermally-administered agents like pharmaceutical solution, emulsion, and cream. Since sapogenol is powder, the form of solid preparation is desirable.

There is no particular limitation on the intake method when the composition of the present invention is used as a pharmaceutical. For example, the method includes oral intake, transdermal intake, and the like. In terms of less burden on patients, oral intake of tablets, capsules, and the like is preferable.

When the composition of the present invention is used as a pharmaceutical, the intake may be established appropriately depending on symptoms, but generally, when it is used as a preventive, the intake of menaquinone-7 per day may be usually 10 μg to 100 mg, preferably 20 μg to 100 mg, and more preferably 5 to 50 mg. When it is used as a therapeutic agent, it can be used with the intake of 1 to 150 mg.

When the composition of the present invention is used as a pharmaceutical, the intake may be established appropriately depending on symptoms, but generally, when it is used as a preventive, the intake of sapogenol per day is preferably 0.1 to 100 mg, and more preferably 5 to 50 mg. When it is used as a therapeutic agent, the intake is preferably 5 to 1,200 mg, and more preferably 150 to 900 mg.

When the composition of the present invention is used as a pharmaceutical, the intake may be established appropriately depending on symptoms, but generally, when it is used as a preventive, the intake of collagen hydrolysate per day is preferably 0.1 to 15 g, and more preferably 1 to 10 g. When it is used as a therapeutic agent, the intake is preferably 0.1 to 20 g, and more preferably 1 to 15 g.

When the composition of the present invention is used as a cosmetic material, apart from the essential components, materials used for general purpose as aids to cosmetics may be added. They include, for example, polyhydric alcohol such as ethylene glycol, polyethylene glycol, propylene glycol, 1,3-butylene glycol, 1,4-butylene glycol, dipropylene glycol, glycerin, diglycerine, polyglycerin, pentylene glycol, isoprene glycol, glucose, maltose, fructose, xylitol, sorbitol, maltotriose, and erythritol; lower alcohol such as methanol, ethanol, propyl alcohol, isopropyl alcohol, butyl alcohol, and isobutyl alcohol; higher fatty acids such as oleic acid, isostearic acid, lauric acid, myristic acid, palmitic acid, stearic acid, behenic acid, and undecylenic acid; fats and oils, such as olive oil, corn oil, *camellia* oil, macadamia nut oil, avocado oil, rapeseed oil, sesame oil, castor oil, safflower oil, cottonseed oil, jojoba oil, coconut oil, and palm oil; waxes such as carnauba wax, candelilla wax, bees wax, and lanolin; saccharides such as sorbitol, mannitol, glucose, sucrose, lactose, and trehalose; thickeners such as carrageenan, xanthan gum, gelatin, pectin, agarose, alginate, dextrin, methylcellulose, ethylcellulose, hydroxypropyl cellulose, hydroxyethyl cellulose, carboxymethyl cellulose, carboxyvinyl polymer, polyvinyl alcohol, polyvinylpyrrolidone, gum arabic, karaya gum, Tragacanth gum, and tamarind gum; preservatives such as phenoxyethanol, methylparaben, ethylparaben, propylparaben, butylparaben, parahydroxybenzonate, benzoic acid, salicylic acid and salts thereof, sorbic acid and salts thereof, dehydroacetic acid and salts thereof, chlorocresol, and hexachlorophene; nonionic surfactants such as sodium lauroyl sulfate and polyoxyethylene sorbitan monooleate, anionic surfactants such as alkyl sulfate salt and normal dodecyl sodium benzenesulfonate, and cationic surfactants such as polyoxyethylene dodecylmonomethylammonium chloride; steroidal and nonsteroidal antiinflammatory agents; vitamins such as vitamin A, vitamin D, vitamin E, vitamin F, and vitamin K and vitamin derivatives such as pyridoxine dicaprylate, pyridoxine dipalmitate, ascorbyl dipalmitate, ascorbyl monopalmitate, and ascorbyl monostearate; antioxidants such as flavonoid and carotenoid; higher aliphatic hydrocarbons such as squalane, squalene, and liquid paraffin; sphingolipids such as ceramide, cerebroside, and sphingomyelin; sterols such as cholesterol and phytosterol; silicones such as methyl polysiloxane, methylphenylpolysiloxane, methylcyclopolysiloxane, octamethyl cyclotetrasiloxane, octamethyl cyclopentasiloxane, decamethyl cyclopentasiloxane, and methyl hydrogen polysiloxane; ultraviolet absorbing agents such as para-aminobenzoic acid, para-aminobenzoic acid monoglyceryl ester, methyl anthranilate, homomenthyl-N-acetyl anthranilate, octyl para-methoxycinnamate, and ethyl-4-isopropyl cinnamate; minerals such as bentonite, smectite, beidellite, nontronite, saponite, hectorite, sauconite, and stevensite; inorganic pigments such as red iron oxide, yellow iron oxide, black iron oxide, cobalt oxide, ultramarine blue, iron blue, titanium oxide, and zinc oxide; coloring agents such as Red No. 202, Yellow No. 4, and Blue No. 404; flavor; and balm.

To use the composition of the present invention as a cosmetic, it is processed into the forms of percutaneously administered agents such as solution, pharmaceutical solution, emulsion, milky liquid, cream, and powder; or of orally administered agents, for example, solid preparations such as powder, granule, capsule, pill, tablet, chewable tablet, and drop, and liquid preparations such as drink, pharmaceutical solution, suspension, emulsion, syrup, and dry syrup.

The intake method when the composition of the present invention is used as a cosmetic is oral intake or transdermal intake. Transdermal administration of pharmaceutical solution, emulsion, milky liquid, or cream is preferable in terms of immediate effects as a cosmetic.

For the intake when the composition of the present invention is used as a cosmetic material, the intake of vitamin K per day is preferably 0.01 to 50 mg, and more preferably 0.01 to 1 mg, by considering symptoms and safety. The intake of sapogenol per day is preferably 0.001 to 100 mg, and more preferably 0.05 to 50 mg. The intake of collagen hydrolysate per day is preferably 0.001 to 20 g, and more preferably 0.01 to 10 g.

Formulation Examples of the present invention will be shown below. However, the present invention is not limited to the following Formulation Examples.

Formulation Example 1

Tablets

TABLE 1

| Composition | Additive amount (parts by weight) |
| --- | --- |
| Cornstarch | 40 |
| Crystalline cellulose | 20 |
| Carboxymethyl cellulose | 10 |
| Menaquinone-7 | 0.01 |
| Sapogenol | 0.1 |
| Collagen hydrolysate | 10 |
| Lactose | Balance |
| Total | 100 |

Formulation Example 2

Capsules

TABLE 2

| Composition | Additive amount (parts by weight) |
| --- | --- |
| Olive oil | 80 |
| Beeswax | 2 |
| Glycerin | 2 |
| Menaquinone-7 | 0.01 |
| Sapogenol | 0.1 |
| Collagen hydrolysate | 10 |
| Lactose | Balance |
| Total | 100 |

Formulation Example 3

Lotions

TABLE 3

| Composition | Additive amount (parts by weight) |
| --- | --- |
| Ethanol | 10 |
| Glycerin | 3 |
| Propylene glycol | 3 |

TABLE 3-continued

| Composition | Additive amount (parts by weight) |
| --- | --- |
| Menaquinone-7 | 0.001 |
| Sapogenol | 0.05 |
| Collagen hydrolysate | 3 |
| Flavor and preservative | q.s. |
| Purified water | Balance |
| Total | 100 |

Formulation Example 4

Creams

TABLE 4

| Composition | Additive amount (parts by weight) |
| --- | --- |
| Squalane | 10 |
| Glycerin | 10 |
| Liquid paraffin | 5 |
| Cetanol | 3 |
| Stearic acid | 2 |
| Lanolin | 2 |
| Menaquinone-7 | 0.5 |
| Sapogenol | 0.05 |
| Collagen hydrolysate | 5 |
| Flavor and preservative | q.s. |
| Purified water | Balance |
| Total | 100 |

EXAMPLES

The present invention will be described in more detail below by way Examples, but the present invention is not limited to the following Examples.

Example 1

1. Preparation of Composition (Skin Function Improving Agent)

Menaquinone-7, collagen hydrolysate, and soyasapogenol were prepared. For menaquinone-7, after a commercial menaquinone-7 reagent (manufactured by Wako Pure Chemical Industries, Ltd.) was subjected to a purity test with HPLC, menaquinone-7 with purity of 99.6% was used.

For collagen hydrolysate, a commercial collagen hydrolysate (product name: collagen tripeptide, manufactured by JELLICE Co., Ltd.) was used. The molecular weight distribution of the collagen hydrolysate is shown in Table 5.

TABLE 5

| Molecular weight range | Proportion (%) |
| --- | --- |
| not less than 6,000 | 3 |
| from 3,000 to less than 6,000 | 15 |
| from 1,000 to less than 3,000 | 48 |
| from 500 to less than 1,000 | 12 |
| from 200 to less than 500 | 8 |
| less than 200 | 14 |
| Total | 100 |

The content of tripeptide (molecular weight of 200 to 1,000) was 20%.

For soyasapogenol, a commercial soyasaponin preparation (product name: saponin B-50, manufactured by J-OIL-MILLS, Inc.) was used. This product contained 27.4% of the saponin A group and 52.3% of the saponin B group. To 750 g of this product, 7.5 L of 80% ethanol containing 2N sulfuric acid was added, and the mixture was incubated at 75° C. for 25 hours. After incubation, 7.5 L of water was added to the reaction mixture to centrifuge. Into the residue after centrifugation, 7.5 L of water was added to neutralize with 1N KOH. Further centrifugation was performed, further water was added from above of the centrifuge, and the mixture was dried to obtain a powder of 251.5 g.

The soyasapogenol concentration in the powder was measured based on the method by Rupasinghe et al. (J. Agric. Food. Chem. 51. 5888-5894, 2003). The results showed that 19.6% for soyasapogenol A and 45.8% for soyasapogenol B.

In addition to the reference diet, the test substances shown in Table 6 were administered to the study groups in Examples and Comparative Examples. By dissolving the test substances in a 0.5% carboxymethyl cellulose sodium solution (hereinafter referred to as CMC-Na solution), the composition (skin function improving agent) was prepared.

The amount of combination of the test substances and the composition was prepared so that the dose of the 0.5% CMC-Na solution was 0.05 mL per 10 g of body weight and so that the dose of the test substances was the value shown in Table 1.

2. Administration Test

Forty two hairless mice Hos:HR1 (male, 5-week old) were prepared. Through the 1-week acclimation period and the test period, the mice were freely fed a reference diet (product name: CRF-1, manufactured by Oriental Yeast Co., Ltd.) and water. The insolation condition was set to day and night every 12 hours. After the acclimation period, grouping of 6 mice/group was performed so that the body weight between groups was homogenous.

Continuous and forced intragastric administration of the above composition was performed to the mice once a day for 28 days using a stomach tube. The reference diet and 0.05 mL per 10 g of body weight of a 0.5% CMC-Na solution were administered to the control group.

TABLE 6

| | Test substance | Dose of test substance |
| --- | --- | --- |
| Control | — | — |
| Comparative Example 1 | Menaquinone-7 | 10 mg/kg of body weight |
| Comparative Example 2 | Collagen tripeptide | 80 mg/kg of body weight |
| Comparative Example 3 | Soyasapogenol | 50 mg/kg of body weight |
| Example 1 | Menaquinone-7 Collagen hydrolysate | 10 mg/kg of body weight 80 mg/kg of body weight |
| Example 2 | Menaquinone-7 Soyasapogenol | 10 mg/kg of body weight 50 mg/kg of body weight |
| Example 3 | Collagen hydrolysate Soyasapogenol | 80 mg/kg of body weight 50 mg/kg of body weight |

3. Evaluation of Skin Function Improving Agent (1) Transdermal Moisture Loss-Inhibiting Function By measuring TEWL values, the transdermal moisture loss-inhibiting function (i.e., skin barrier function) of the composition (skin function improving agent) was evaluated. In measurement of TEWL, a commercial tewameter (product name: TM300, manufactured by Integral Corporation)

was used. The back of the mice was used for the measurement site. Measurement was performed on the day before test substance administration and days 14 and 28 after administration.

FIGS. 1A to 1C show the values in which the transepidermal water loss on the day before test substance administration is subtracted from the transepidermal water loss on day 28 after test substance administration. A significance test of measurement results was performed by Tukey's multiple comparison test. In the figures, * and ** represent the case in which there is a significant difference with a significance level (P) of P<0.05 and P<0.01, respectively.

FIG. 1B shows that decreases in the transepidermal water loss were significantly inhibited compared with that in the control group in Example 2 (menaquinone-7 and soyasapogenol) (P<0.05). Also in Example 1 (menaquinone-7 and collagen hydrolysate) in FIG. 1A and Example 3 (collagen hydrolysate and soyasapogenol) in FIG. 1C, a tendency to inhibit the transepidermal water loss was observed. These findings reveal that a skin function improving agent of the present invention, especially a skin function improving agent containing menaquinone-7 and soyasapogenol, is effective for inhibiting moisture loss in the sebaceous membrane.

(2) Stratum Corneum Water-Retaining Function

The keratin usually contains 20% to 30% of water. It is considered that a lower amount of moisture in the keratin is associated with decreases in water in the stratum corneum or a natural moisturizing factor (NMF) involved in water retention, resulting in dryness of the skin. By measuring the moisture in the keratin, the stratum corneum water-retaining function (i.e., skin moisture-retaining function) of a skin function improving agent can be evaluated.

In measurement of the moisture in the keratin, a commercial corneometer (product name: CM825, manufactured by Integral Corporation) was used. The back of the mice was used for the measurement site. Measurement was performed on the day before test substance administration and days 14 and 28 after administration.

FIGS. 2A to C show the values in which the reference of the moisture in the keratin on the day before test substance administration is subtracted from the moisture in the keratin on day 28 after test substance administration. A significance test of measurement values was performed by Tukey's multiple comparison test. In the figures, * and ** represent the case in which there is a significant difference with a significance level (P) of P<0.05 and P<0.01, respectively.

FIG. 2A shows that the use of menaquinone-7 or collagen hydrolysate alone does not exert the keratin water-retaining function. However, as in the present invention, combination of menaquinone-7 and collagen hydrolysate exerts the keratin water-retaining function. This finding reveals that a skin function improving agent of the present invention containing menaquinone-7 and collagen hydrolysate is effective for retaining moisture in the stratum corneum.

FIG. 2B shows that the use of menaquinone-7 alone does not exert the stratum corneum water-retaining function, but the use of soyasapogenol alone exerts the function. As in the present invention, even combination of menaquinone-7 and soyasapogenol exerts the keratin water-retaining function.

What is claimed:

1. A composition comprising vitamin K and at least one component selected from the group consisting of sapogenol and collagen hydrolysate.

2. The composition according to claim 1, wherein the vitamin K is vitamin K2.

3. The composition according to claim 2, wherein the vitamin K2 is menaquinone-7.

4. The composition according to claim 1, wherein the sapogenol is derived from soybean.

5. The composition according to claim 1, wherein a content of peptide having a molecular weight from 200 to less than 3,000 in the collagen hydrolysate is not less than 40% by mass.

6. A skin function improving agent comprising the composition according to claim 1 as an active ingredient.

7. The skin function improving agent according to claim 6, which includes vitamin K and sapogenol, wherein the skin function is a transdermal moisture loss-inhibiting function.

8. The skin function improving agent according to claim 6, which includes vitamin K and collagen hydrolysate, wherein the skin function is a function of retaining the moisture in the stratum corneum.

* * * * *